(12) United States Patent
Cohlmia, Jr.

(10) Patent No.: US 11,896,212 B2
(45) Date of Patent: Feb. 13, 2024

(54) PERCUTANEOUS LARGE HOLE PROCEDURE

(71) Applicant: George S. Cohlmia, Jr., Tulsa, OK (US)

(72) Inventor: George S. Cohlmia, Jr., Tulsa, OK (US)

( * ) Notice: Subject to any disclaimer, the term of this patent is extended or adjusted under 35 U.S.C. 154(b) by 158 days.

(21) Appl. No.: 17/817,624

(22) Filed: Aug. 4, 2022

(65) Prior Publication Data

US 2023/0027775 A1 Jan. 26, 2023

Related U.S. Application Data

(63) Continuation-in-part of application No. 16/502,308, filed on Jul. 3, 2019, now abandoned, which is a continuation-in-part of application No. 15/403,979, filed on Jan. 11, 2017, now abandoned, which is a continuation-in-part of application No. 15/197,003, filed on Jun. 29, 2016, now abandoned, which is a continuation-in-part of application No. 14/977,956, filed on Dec. 22, 2015, now abandoned.

(60) Provisional application No. 62/095,266, filed on Dec. 22, 2014.

(51) Int. Cl.
  *A61B 17/10* (2006.01)
  *A61B 17/04* (2006.01)
  *A61B 17/08* (2006.01)

(52) U.S. Cl.
  CPC .......... *A61B 17/0466* (2013.01); *A61B 17/08* (2013.01); *A61B 17/10* (2013.01)

(58) Field of Classification Search
  CPC ............ A61B 17/0057; A61B 17/0466; A61B 17/064; A61B 17/068; A61B 17/08; A61B 17/083; A61B 17/10; A61B 17/105; A61B 2017/00584; A61B 2017/00663; A61B 2017/00668; A61B 2017/086; A61B 2017/1142
  USPC ......................................................... 606/213
  See application file for complete search history.

(56) References Cited

U.S. PATENT DOCUMENTS

| | | | |
|---|---|---|---|
| 8,590,760 B2 * | 11/2013 | Cummins .......... | A61B 17/0684 606/139 |
| 2012/0143226 A1 * | 6/2012 | Belson ............... | A61B 17/0057 606/139 |
| 2012/0158050 A1 * | 6/2012 | Woods ............... | A61B 17/0401 606/232 |

(Continued)

*Primary Examiner* — Melanie R Tyson
(74) *Attorney, Agent, or Firm* — Hall Estill Law Firm

(57) ABSTRACT

A set of devices and associated methodology for percutaneously closing a puncture through the wall of an artery. The method includes inserting a guide wire through a percutaneous entry and into the artery; using the guide wire to guide an insertion of an introducer catheter into the artery; inserting a balloon catheter through the introducer catheter and into the artery; obtaining a tube having a clamp configured to selectively clamp to the introducer catheter; loading the tube with a plurality of fasteners, each fastener individually tethered to a suture; clamping the tube loaded with fasteners onto the introducer catheter, thereby aligning the puncture with a distal working end of the tube; ejecting two or more of the fasteners from the tube to attach onto the artery; percutaneously tying together the tethered sutures of the attached fasteners to draw the attached fasteners together, closing the puncture.

1 Claim, 21 Drawing Sheets
(13 of 21 Drawing Sheet(s) Filed in Color)

(56) References Cited

U.S. PATENT DOCUMENTS

2018/0221026 A1\* 8/2018 Blackmon .......... A61B 17/0487
2021/0386425 A1\* 12/2021 Lim .................... A61B 17/083

\* cited by examiner

PERCUTANEOUS LARGE HOLE PROCEDURE

RELATED APPLICATIONS

This is a continuation-in-part of U.S. patent application Ser. No. 16/502,308 filed on Jul. 3, 2019 and now abandoned, which is a continuation-in-part of U.S. patent application Ser. No. 15/403,979 filed on Jan. 11, 2017 and now abandoned, which is a continuation-in-part of U.S. patent application Ser. No. 15/197,003 filed on Jun. 29, 2016 and now abandoned, which is a continuation-in-part of U.S. patent application Ser. No. 14/977,956 filed on Dec. 22, 2015 and now abandoned, which claims benefit of priority from U.S. Provisional Patent Application Ser. No. 62/095,266 filed on Dec. 22, 2014. Each of the applications listed above is hereby expressly incorporated herein by reference in their entirety.

BACKGROUND

The present invention relates generally to postoperative device, system, and method for closing a large puncture hole in a vessel such as an artery, previously made for undergoing diagnostic or interventional catheterization procedures.

Cardiac catheterization is a well-known and common medical procedure used to diagnose and treat some heart conditions. Typically, a long, thin flexible tube called a catheter is put into a blood vessel in the arm, groin, or neck and threaded to the heart. Through the catheter, the doctor can do diagnostic tests and treatments on the heart. After the procedure, the opening made in the blood vessel must obviously be closed and numerous medical devices and procedures have been developed specifically for this type of closure. It is also understood that numerous other procedures other than cardiac catheterization procedures access a blood vessel needing closing such as but not limited to peripheral vascular interventions, radiological intervention procedures, and so forth.

After the procedure to close the opening in the vessel and the suture has been completed, pressure must be applied to the site until proper hemostasis has occurred. This is typically done by placing a hand and or fingers over the site and applying compression pressure. Needless to say, this requires a medical professional to stand and hold for a period of time, which prevents the person from doing other tasks.

Although numerous advancements have occurred in the surgical field in general, the prior art still has failed to bridge the gap between the needs of medical professionals treating vessel wall closures. Therefore, an extensive opportunity for design advancements and innovation remains for compression pressure device, systems, and methods where the prior art fails or is deficient.

SUMMARY

Embodiments of this invention variously contemplate a set of devices and associated methodology to percutaneously close a puncture through the wall of an artery. The method includes inserting a guide wire through a percutaneous entry and into the artery; using the guide wire to guide an insertion of an introducer catheter into the artery; inserting a balloon catheter through the introducer catheter and into the artery; obtaining a tube having a clamp configured to selectively clamp to the introducer catheter; loading the tube with a plurality of fasteners, each fastener individually tethered to a suture; clamping the tube loaded with fasteners onto the introducer catheter, thereby aligning the puncture with a distal working end of the tube; ejecting two or more of the fasteners from the tube to attach onto the artery; percutaneously tying together the tethered sutures of the attached fasteners to draw the attached fasteners together, closing the puncture.

DRAWINGS

The patent file contains at least one drawing executed in color. Copies of this patent or patent application publication with color drawing(s) will be provided by the Office upon request and payment of the necessary fee.

The invention will be better understood when consideration is given to the following detailed description thereof. Such description makes reference to the annexed pictorial illustrations, graphs, drawings and appendices.

FIG. 9 depicts inserting the introducer catheter into the femoral artery on the same wire used for the large bore catheter in FIG. 8;

FIG. 10 depicts locking the firing mechanism onto the inserted introducer catheter;

FIG. 11 is a partial subskin depiction of FIG. 10;

FIG. 12 is an enlarged portion of FIG. 11;

FIG. 13 is similar to FIG. 10 but depicting the firing mechanism rotated about laterally about ninety degrees;

FIG. 14 depicts the introducer catheter withdrawn;

FIG. 15 depicts percutaneously twisting and tying the sutures;

FIG. 16 depicts a pattern of four fasteners 112 fired onto the outer surface of the artery under closure.

DESCRIPTION OF ILLUSTRATIVE EMBODIMENTS

Figure 1:
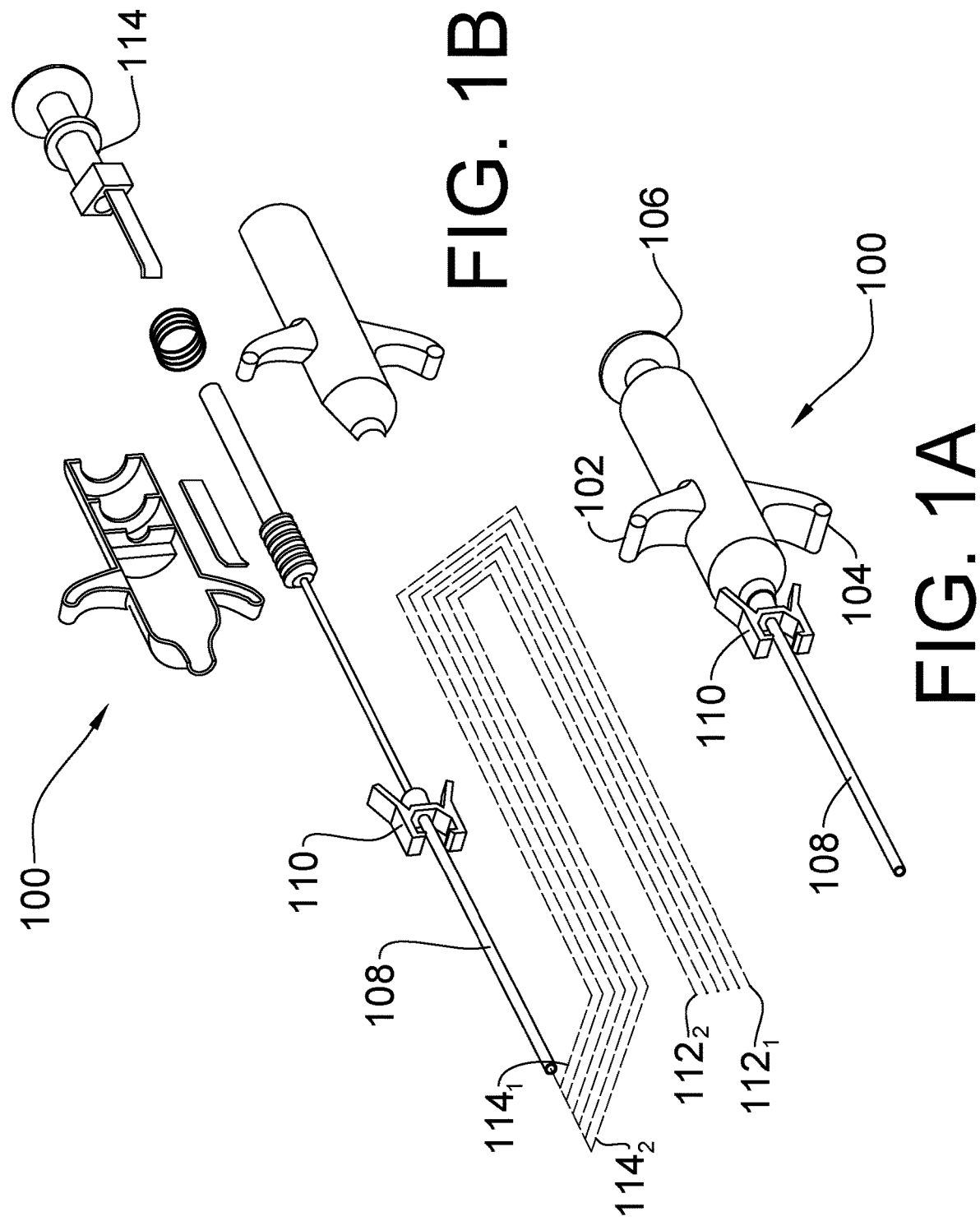
FIG. 1A is an isometric depiction of a firing mechanism constructed in accordance with illustrative embodiments of this invention.
FIG. 1B is an exploded depiction of FIG. 1A.

Referring now to the drawings, wherein like reference numerals designate corresponding structure throughout the views, FIG. 1A is an isometric depiction of a firing mechanism 100 constructed in accordance with illustrative embodiments of this invention. The user grasps the firing mechanism 100 between his fingers and the palm of his hand, fingers pulling on opposing housing wings 102, 104 and his palm pushing against a spring-loaded plunger 106. At the other end is a hollow tube 108 with a clamp 110. The firing mechanism 100 is loaded with a number of fasteners, and configured to enable the user to percutaneously attach each fastener, individually, to the outer surface of an artery. Each of the fasteners is tethered to a respective suture. In these illustrative embodiments the fastener is a staple but that is entirely by way of illustration and not by limitation. FIG. 1B is an exploded view of FIG. 1A, depicting the firing mechanism 100 is loaded in this example with six fasteners $112_1$-$112_6$, each having an individually attached suture $114_1$-$114_6$, all inside the tube 108.

Figure 2:
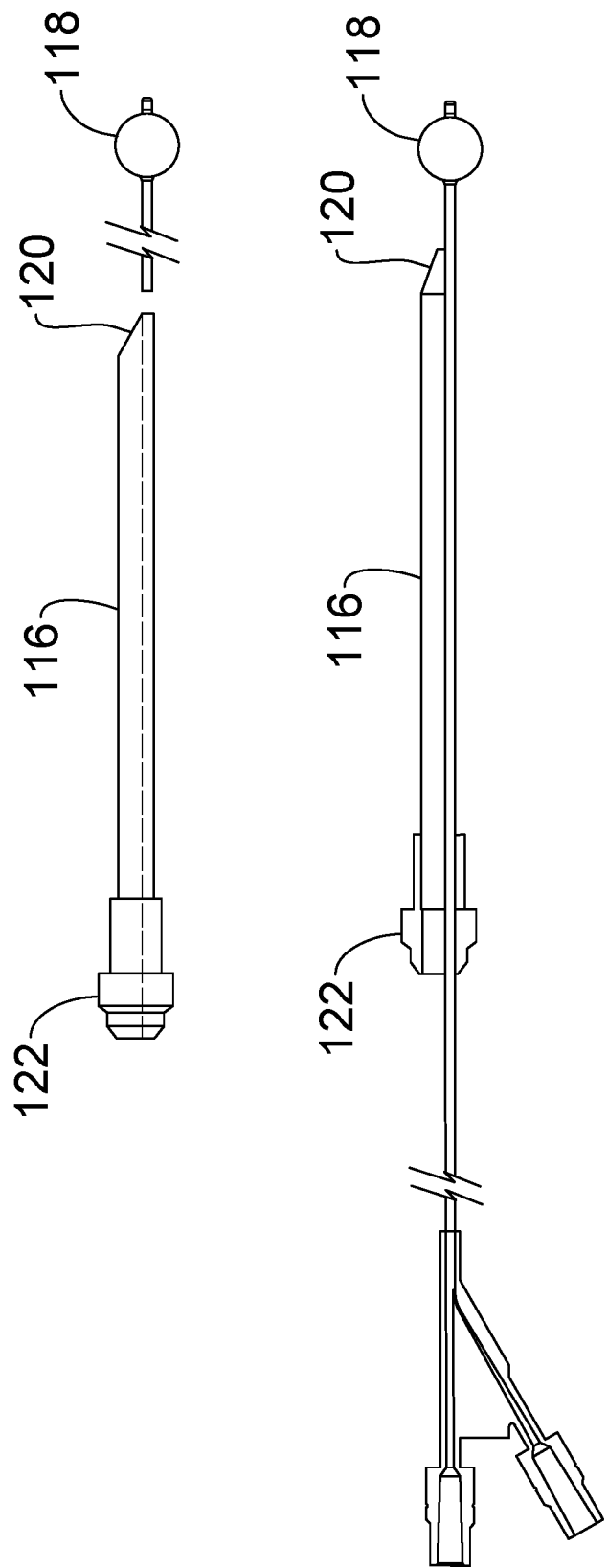
FIG. 2 is a partial cross sectional depiction of an introducer catheter in accordance with illustrative embodiments of this invention.
Figure 3:
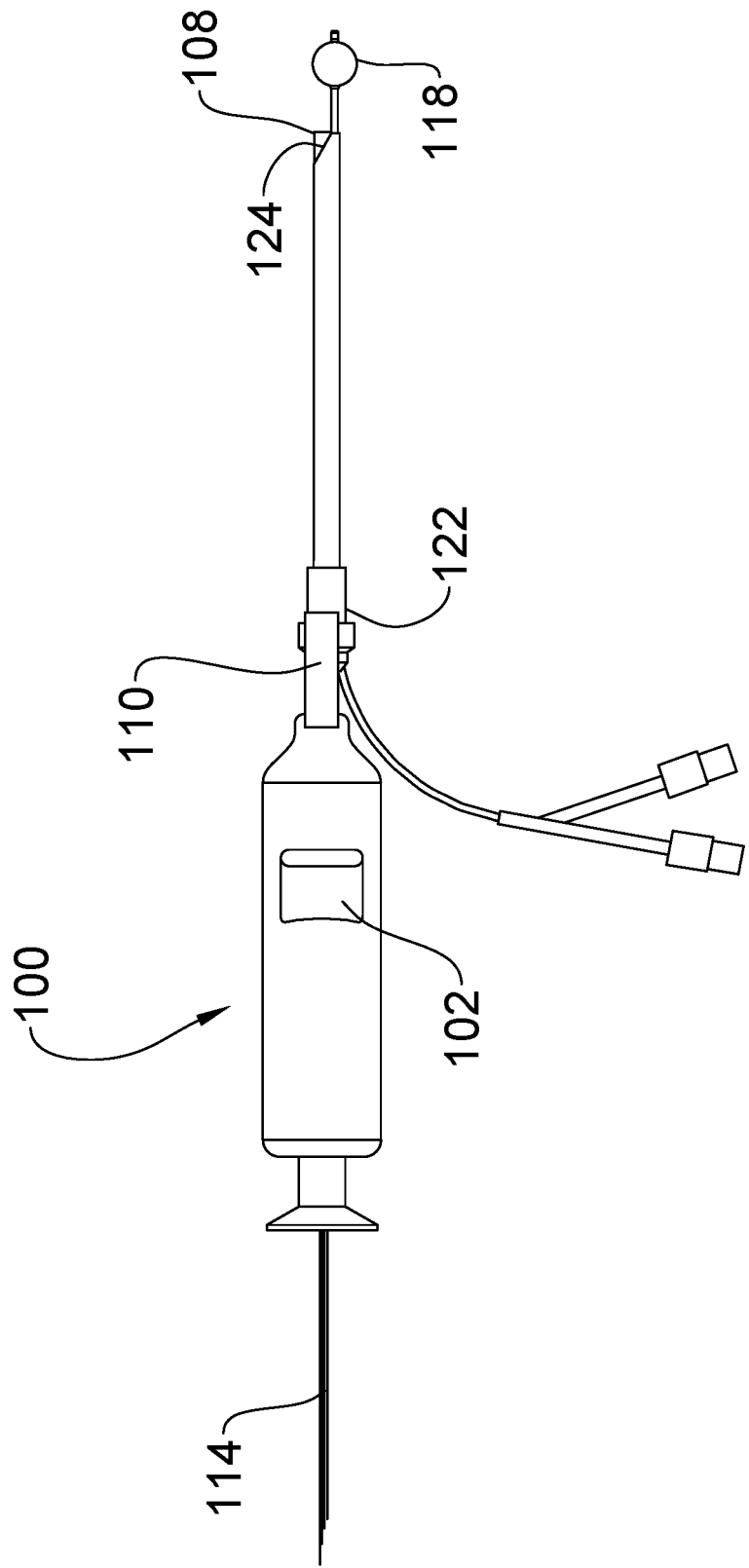
FIG. 3 depicts the firing mechanism of FIG. 1A locked into the introducer catheter of FIG. 2.

FIG. 2 depicts, in partial cross section form, an introducer catheter 116 that is used with the firing mechanism 100 to perform large hole procedures. The introducer catheter 116 defines two separate internal passages. A balloon stent 118 has been placed through one of those passages as depicted, and the other passage 120 is configured to receive the firing mechanism's tube 108 in a close mating engagement. A collar 122 at the entrance is configured to matingly lock with the firing mechanism's clamp 110, and thereby positively position the firing mechanism's tube 108 to the introducer catheter 116. FIG. 3 depicts the firing mechanism 100 attached to the introducer catheter 116, by the clamp 110 closing around the collar 122 in this example. This positions the tube's distal end 124 adjacent the distal end of the introducer catheter 116. Activating the firing mechanism 100 ejects one of the fasteners 112 from the tube 108 and attaches it to the outer surface of an artery. In accordance with this invention as described in the following example, this allows the user to successfully close a large artery puncture by percutaneously positioning each fastener 112 around the puncture opening, so that pulling on and tying together the percutaneously-accessible sutures 114 brings the fasteners 112 together and closes the puncture opening.

Figure 4:
FIGS. 4-8 depict conventional steps in a large bore catheterization procedure.
Figure 5:
Figure 6:
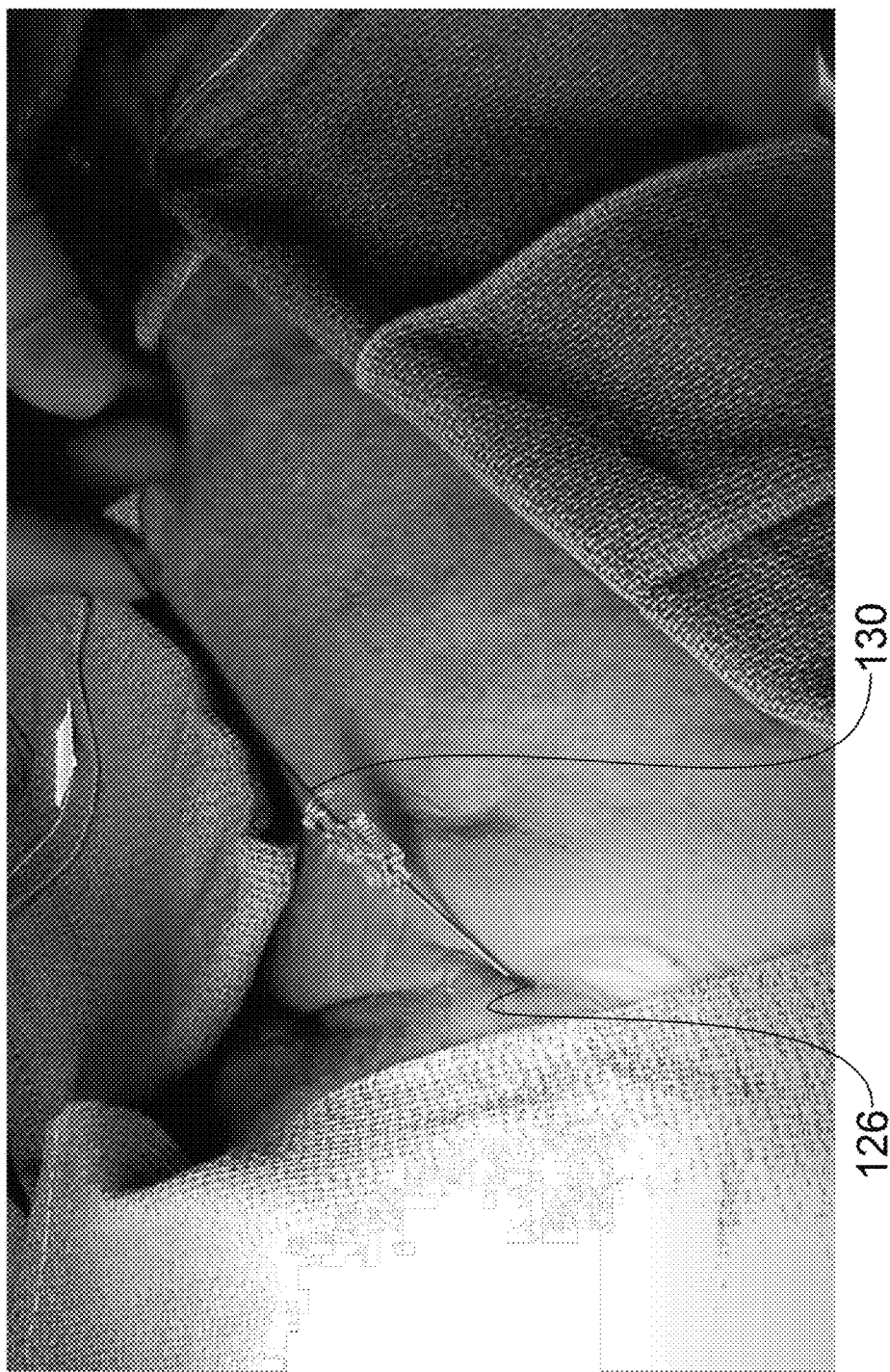
Figure 7:
Figure 8:

Some large artery punctures needing this invention are the result of medical procedures using a large bore catheter. FIG. 4 depicts such a procedure begins by making an incision at the percutaneous entry 126, in this example for entry into the patient's femoral artery. FIG. 5 depicts a needle 128 is inserted through the entry and into the artery. The enables pushing a wire 130 through the needle 128 and into the artery, as depicted in FIG. 6. Finger-pressure is applied to keep the wire 130 in place, while pulling the needle 128 out and away as depicted in FIG. 7. FIG. 8 depicts the inserted wire 130 having been used to guide the insertion of a large bore catheter 132 for the desired medical procedure. After that medical procedure is completed, this invention is employed to close the puncture made by the large bore catheter 132.

Figure 9:
FIGS. 9-16 depict steps in a method for percutaneously closing a large hole in accordance with illustrative embodiments of this invention.

An illustrative percutaneous large hole procedure in accordance with this invention is depicted beginning in FIG. 9 which depicts the large bore catheter 132 having been withdrawn and removed, and then replaced by guiding the introducer catheter 116 on the same already-inserted wire 130 to insert its distal end through the puncture and into the artery. The balloon 118 is passed through the introducer catheter 116 and into the artery. With both the balloon 118 and the introducer catheter 116 inserted in the artery, the balloon 118 is inflated to occlude the artery.

As best depicted in FIG. 2, this also aligns the artery's center below the center of the passage 120 (FIG. 3) which positions the firing mechanism's distal working end 124. After that alignment is initially achieved, the balloon 118 can be artfully moved transversely in the artery nearer the puncture so that the introducer catheter's distal end can be withdrawn through the puncture, away from the puncture opening edges, as depicted below. By inflating the balloon 118 in close proximity to the puncture opening, and/or by slight transverse pressure, it pushes and pulls on the puncture opening collectively to position it around the firing mechanism's working end 124.

Figure 10:
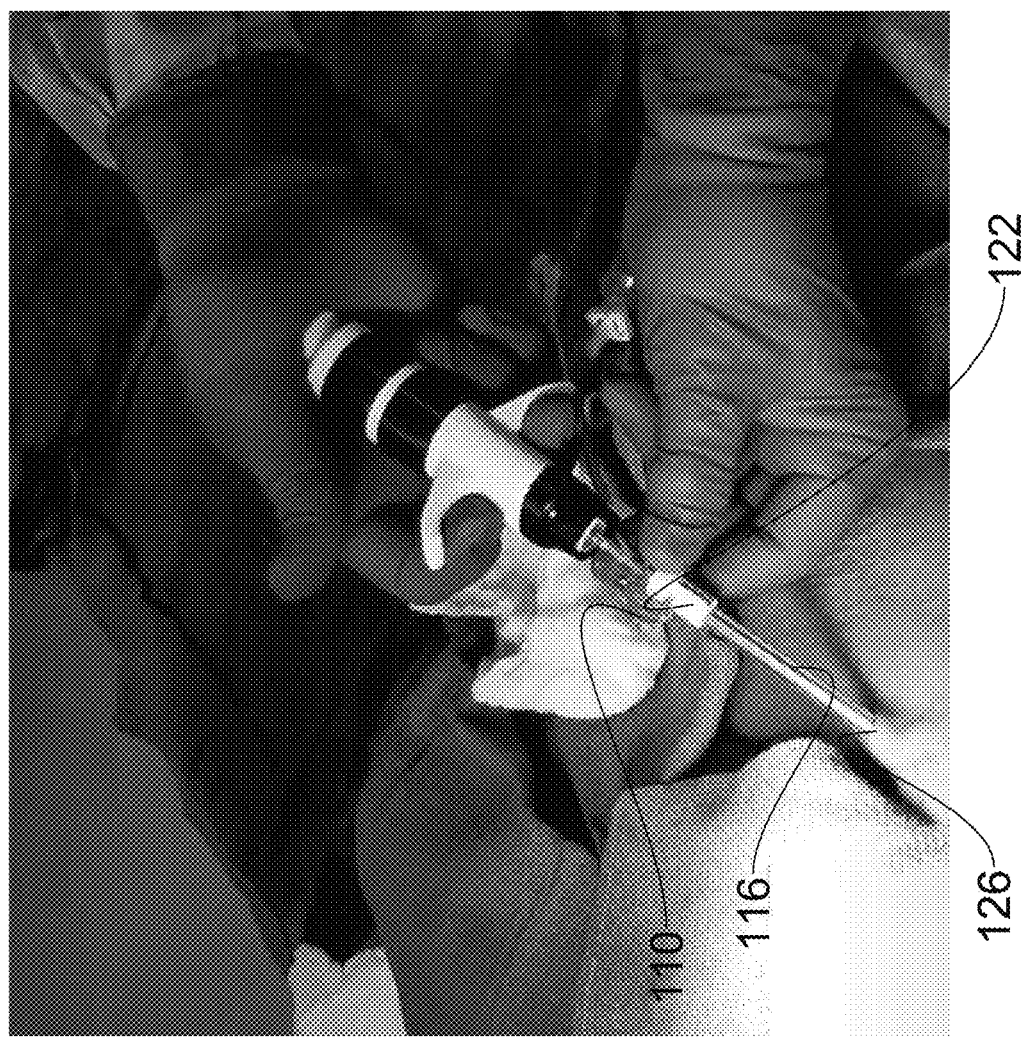
Figure 11:
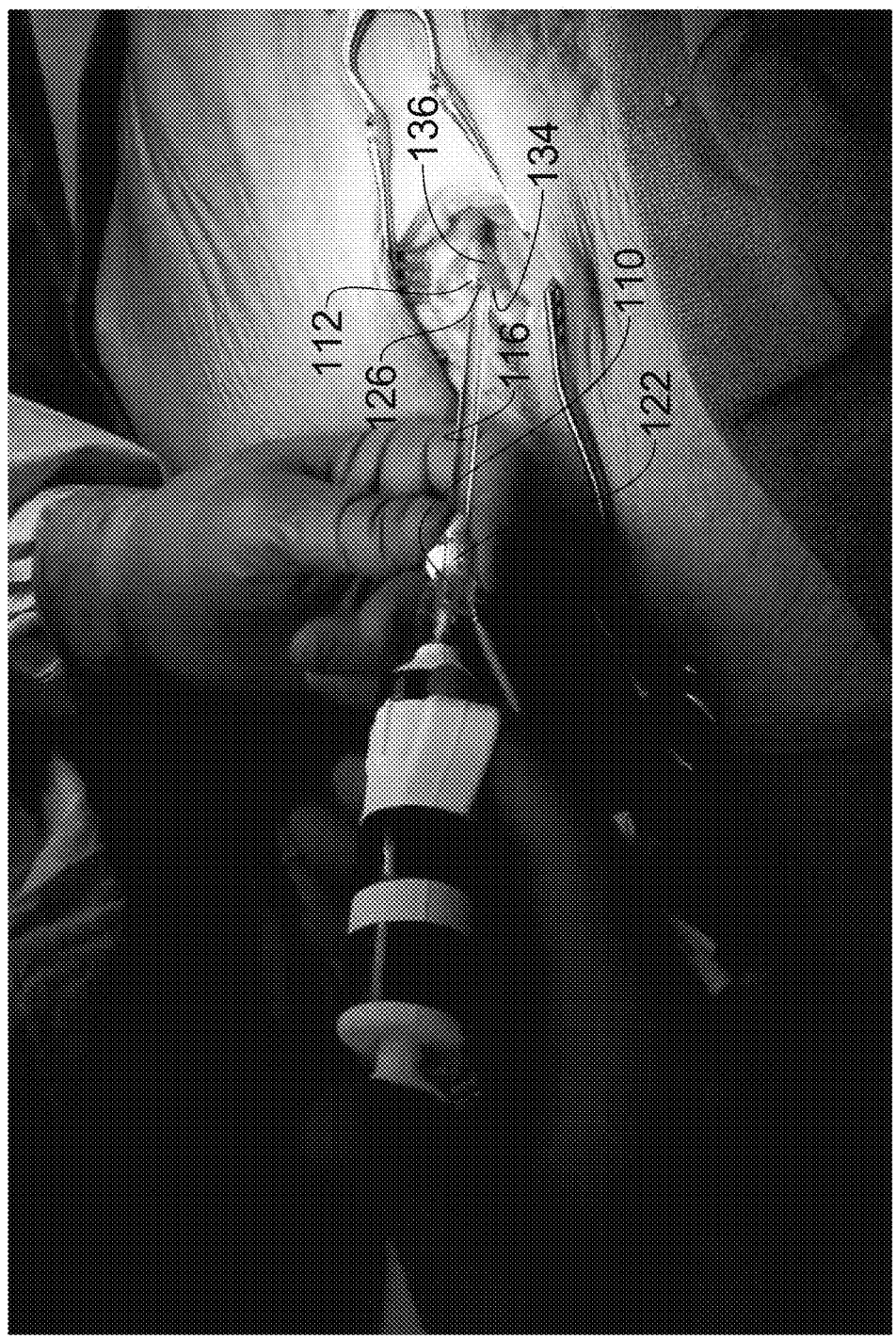
Figure 12:
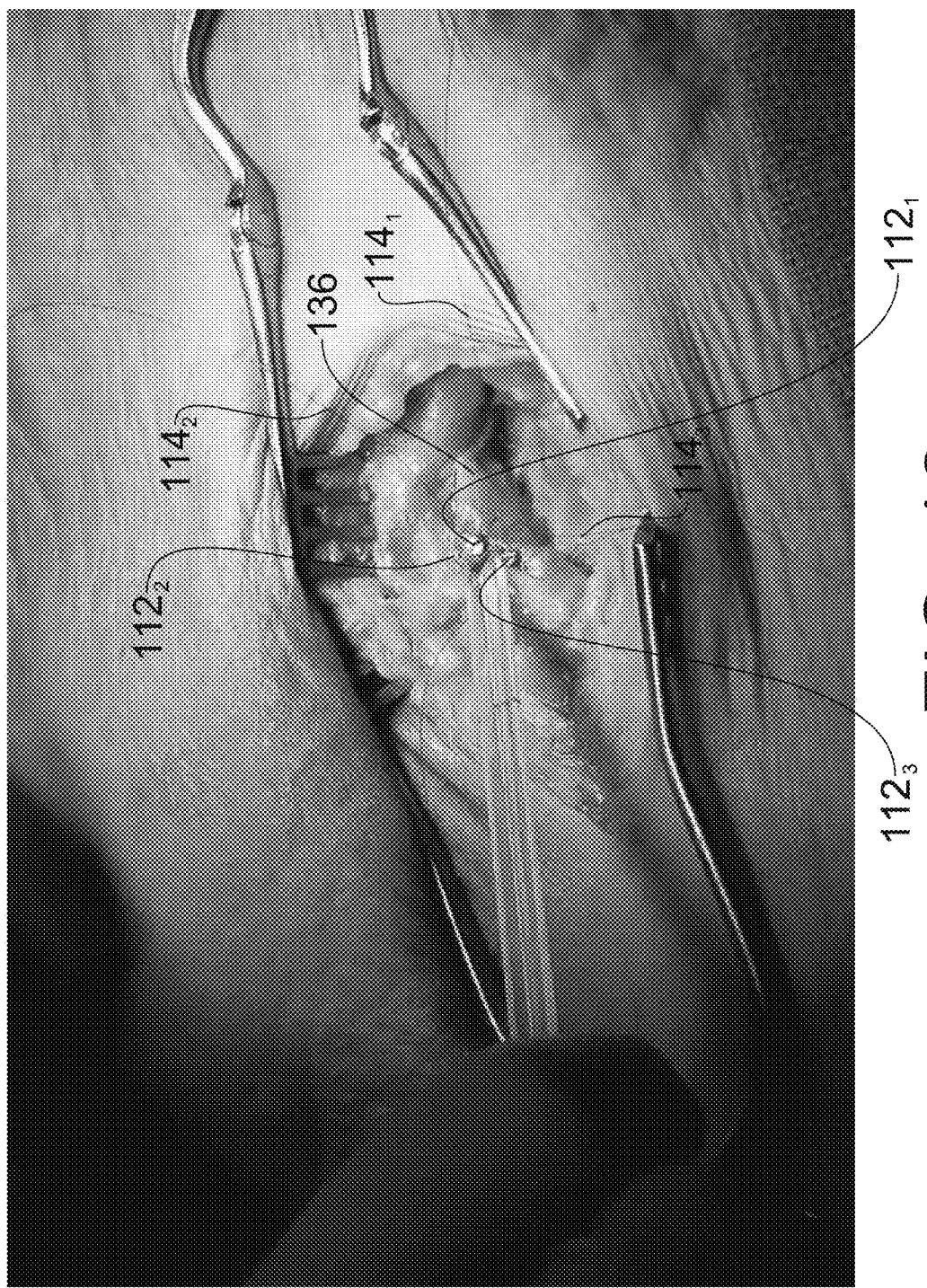
Figure 13:
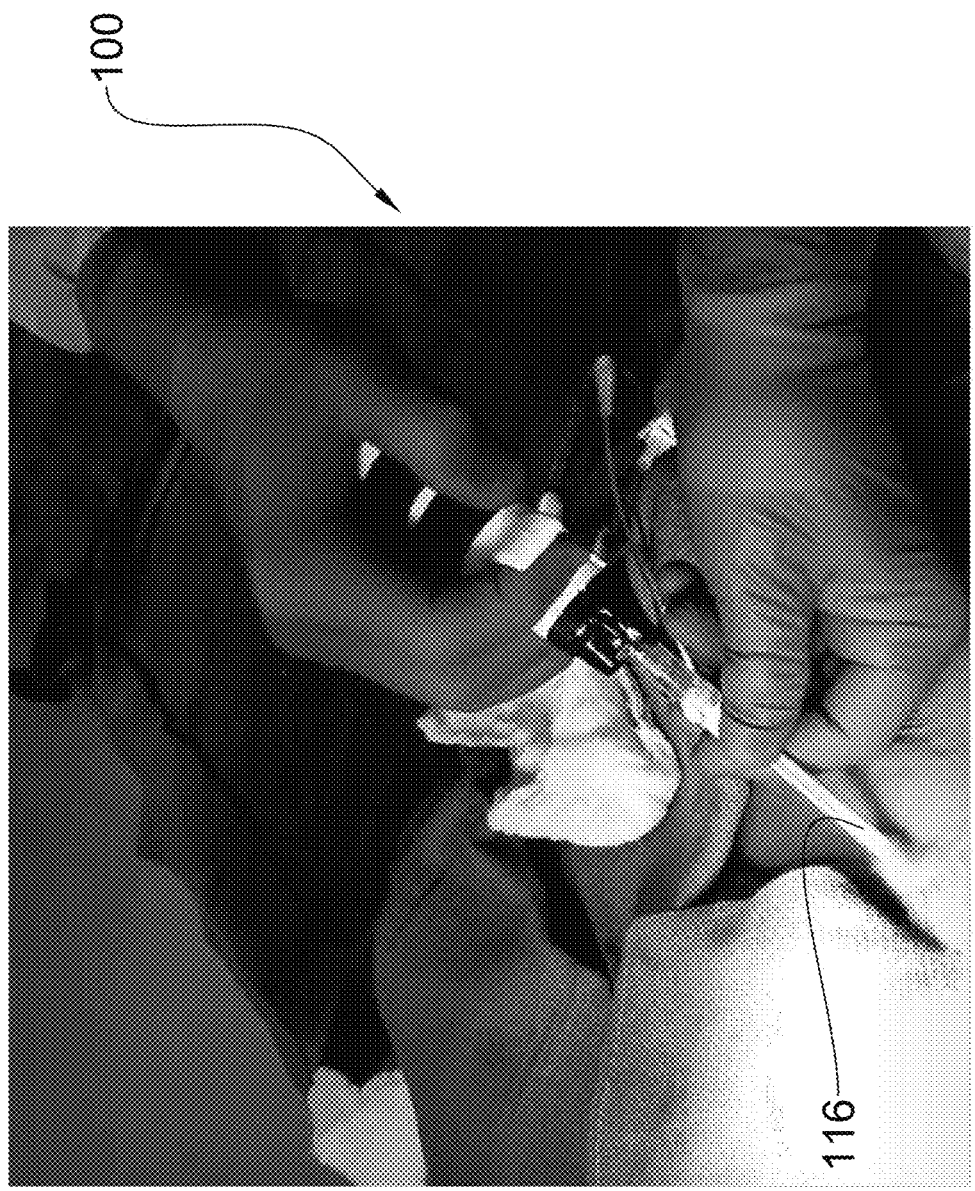

With the introducer catheter 116 so inserted, FIG. 10 depicts the firing mechanism 100 is then locked onto the introducer catheter 116 for percutaneously attaching the loaded fasteners 112 around the puncture opening. FIG. 11 is a partial subskin depiction of one of the fasteners 112 fired onto the artery under closure 136. FIG. 12 is an enlarged depiction of three such fasteners $112_1$, $112_2$, $112_3$ fired onto the artery 136. FIG. 11 also depicts the slanted leading end of the introducer catheter 116 is operably disposed away from a present fastener 112 being fired. The position of the fasteners 112 is determined by the user's selected rotation of the firing mechanism 100. For example, the laterally-disposed fasteners $112_1$, $112_2$ are about ninety degrees apart. FIG. 13 is similar to FIG. 10 except that the firing mechanism 100 is rotated about ninety degrees to get such a fastener pattern.

Figure 14:
Figure 15:
Figure 16:
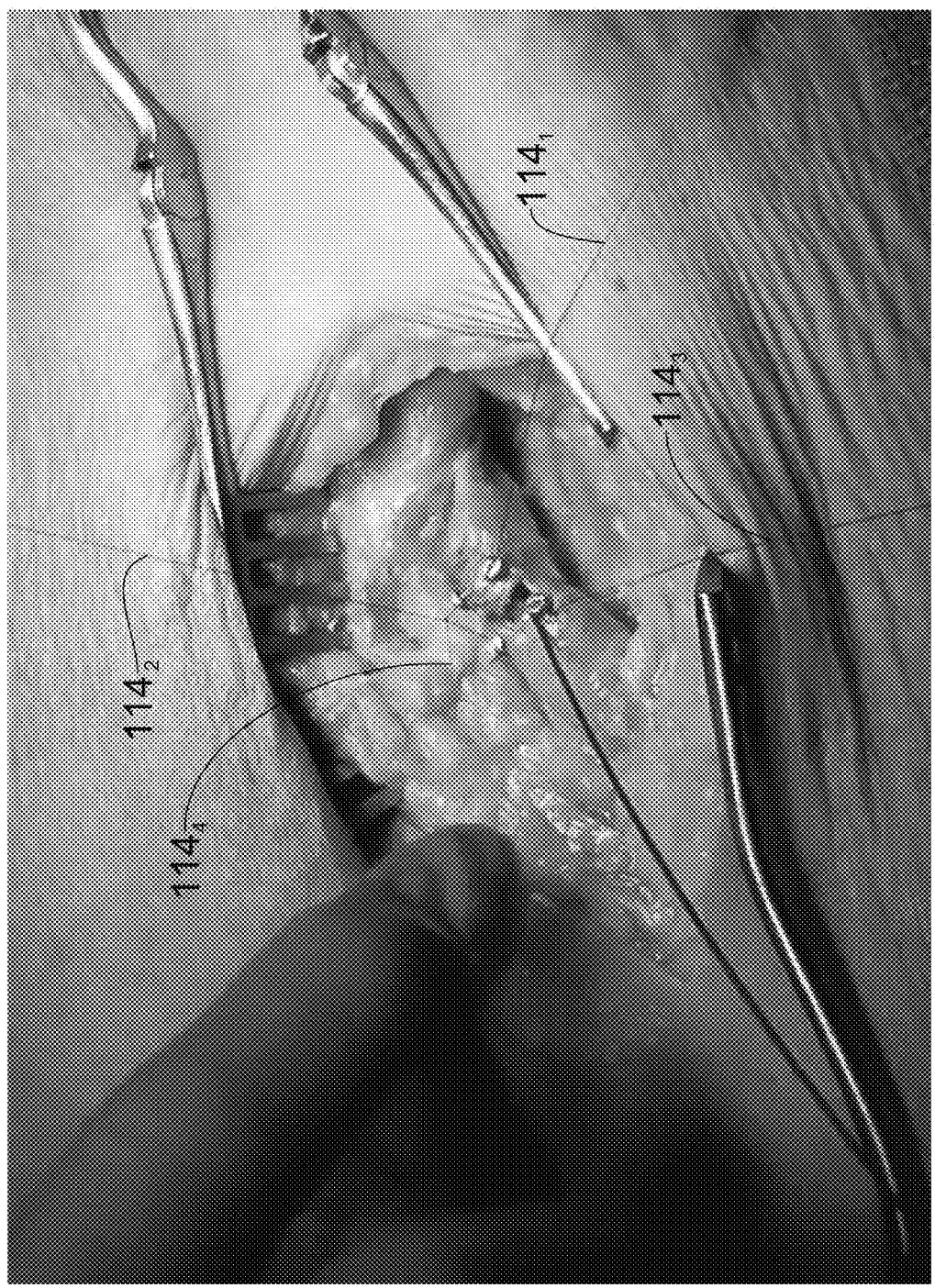

After the desired number of fasteners 112 are fired onto the artery 136, the firing mechanism 100 and the introducer catheter 116 are removed, leaving only the sutures 114 and the wire 130 as depicted in FIG. 14. In FIG. 15 the wire 130 is removed leaving only the sutures extending from the entry 126. The sutures 114 are percutaneously twisted and tied together to draw the fasteners 112 together and thus close the puncture. A tool is depicted in use during that time, such as a knot pusher and/or a hemostasis device as discussed below. FIG. 16 is a subskin depiction of four fasteners 112 fired onto the artery 136 in a pattern of two pair of lateral fasteners on opposing transverse sides of the puncture opening.

Figure 17:
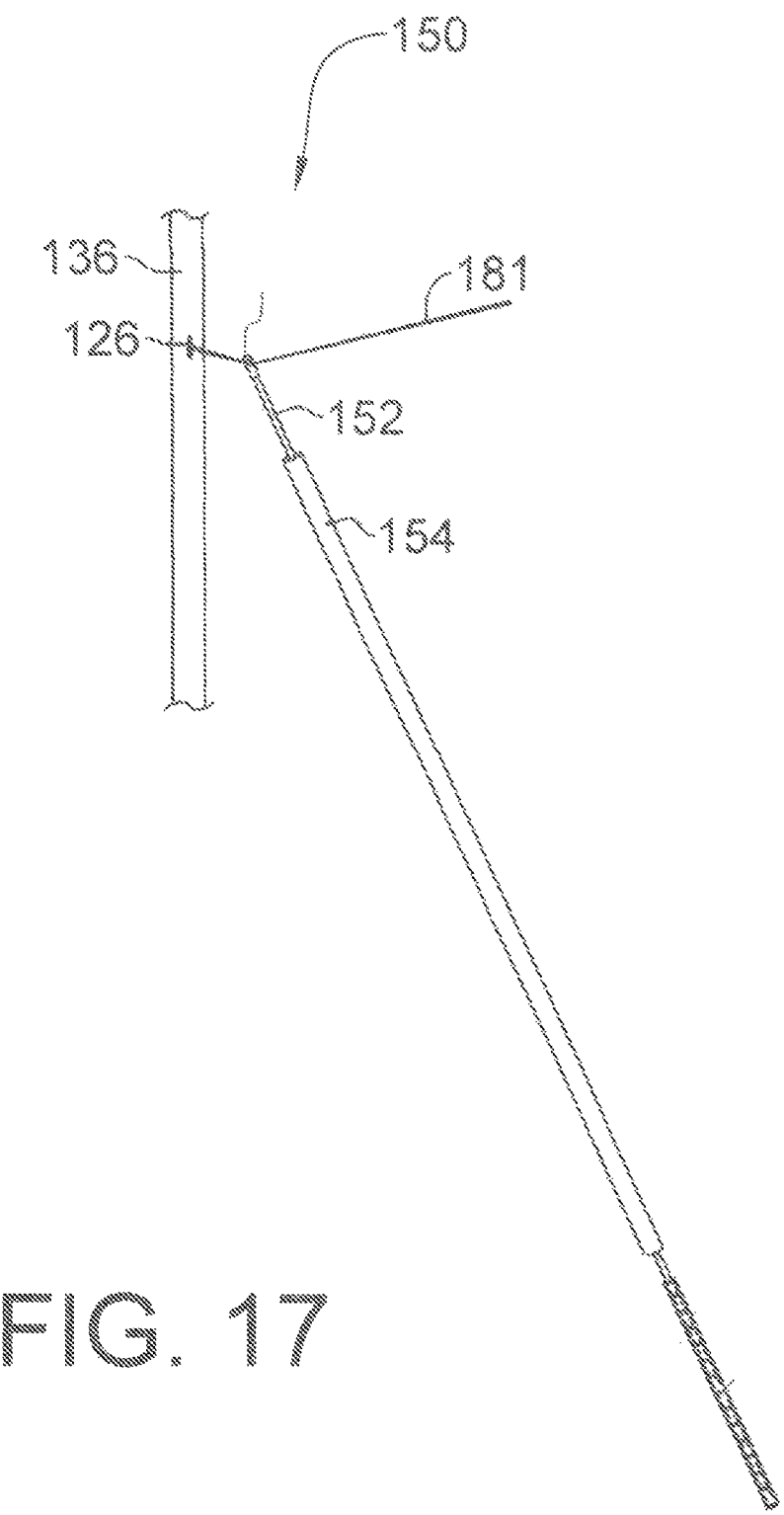
FIG. 17 is generally an illustration depicting a snare attached to a suture in accordance with a preferred embodiment of the current invention.

FIG. 17 depicts one such exemplary tool used to enhance closing the puncture. Reference numeral 150 generally refers to a new and improved postoperative device, system, and method for providing direct pressure to encourage effective hemostasis of a punctured vessel such as but not limited an artery.

Figure 18:
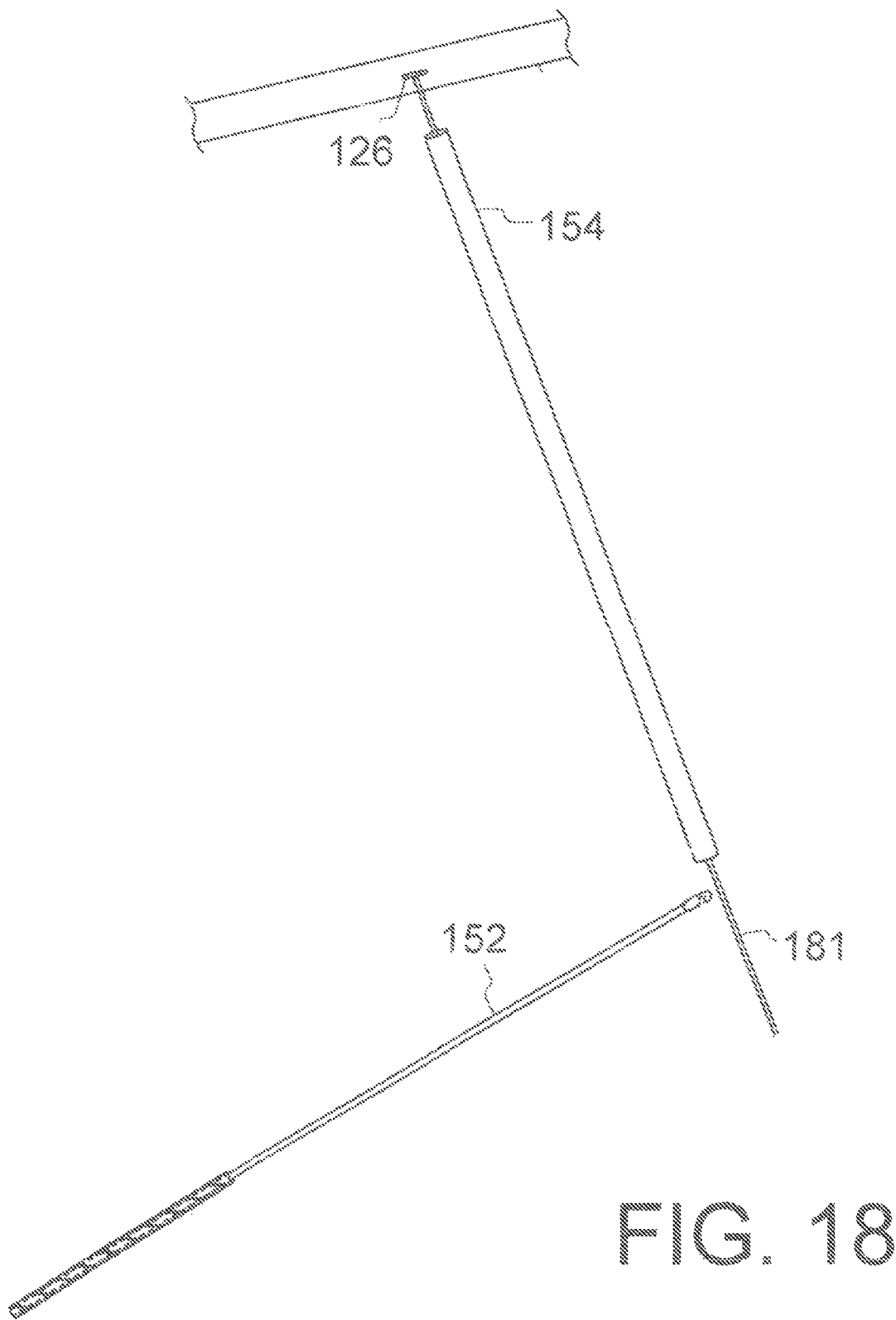
FIG. 18 is generally an illustration depicting a snare removed from the sheath with the suture threaded inside the sheath in accordance with a preferred embodiment of the current invention.
Figure 19:
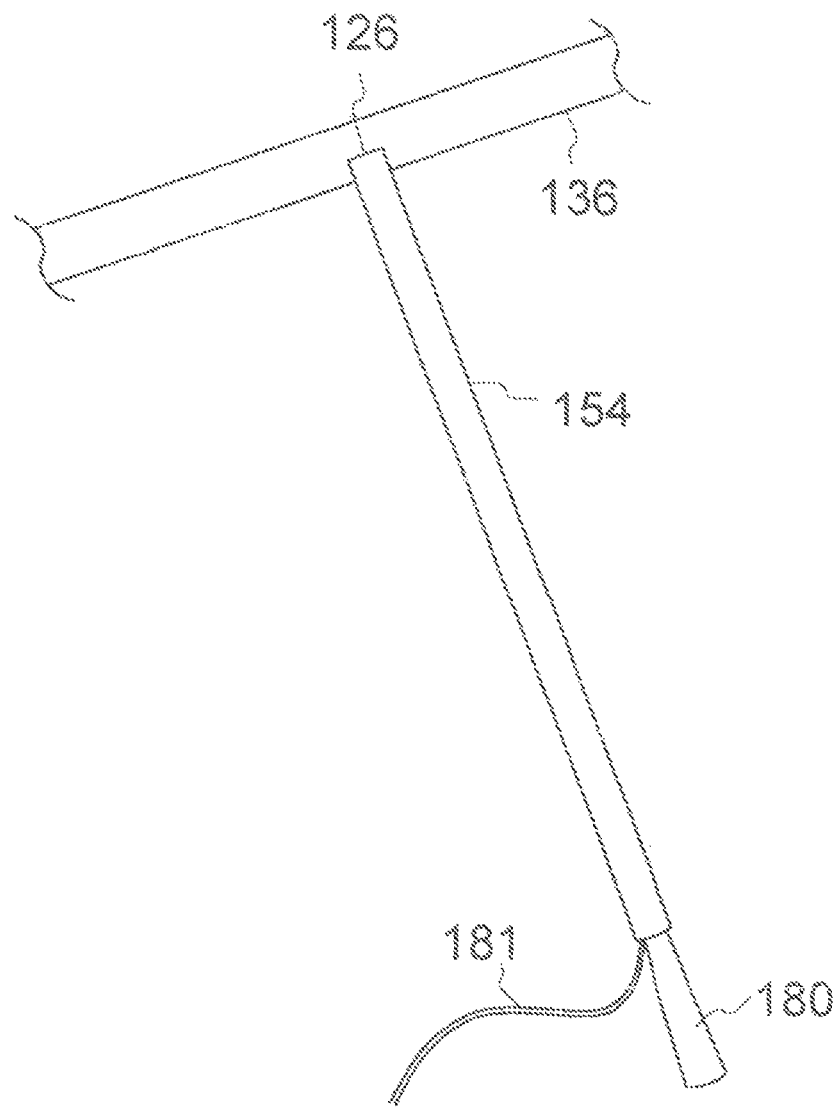
FIG. 19 is generally an illustration depicting the sheath held against the vessel closure site with the suture threaded inside the sheath and held in place with the plug in accordance with a preferred embodiment of the current invention.

Referring to the drawings and more in particular to FIGS. 17, 18, and 19, tool 150 may generally include a snare 152 that cooperatively resides in a stop or sheath 154. Tool 150, snare 152 and sheath 154 may provide direct pressure to access or puncture site 126 of an artery or vessel 136 utilizing existing suture 181 such as but not limited to after closing common femoral artery or vessel access site suture used for the closing for patients who have undergone diagnostic or interventional catheterization procedures. It is understood that tool 150 may be utilized with other procedures, other vessels and so forth. It should not be considered limited to the examples and illustrations. It is also understood that suture 181 may be one or more strands as known in the art and the illustration should not be considered to limit the invention to two and the term "suture" generally refers to two strands.

Figure 20:
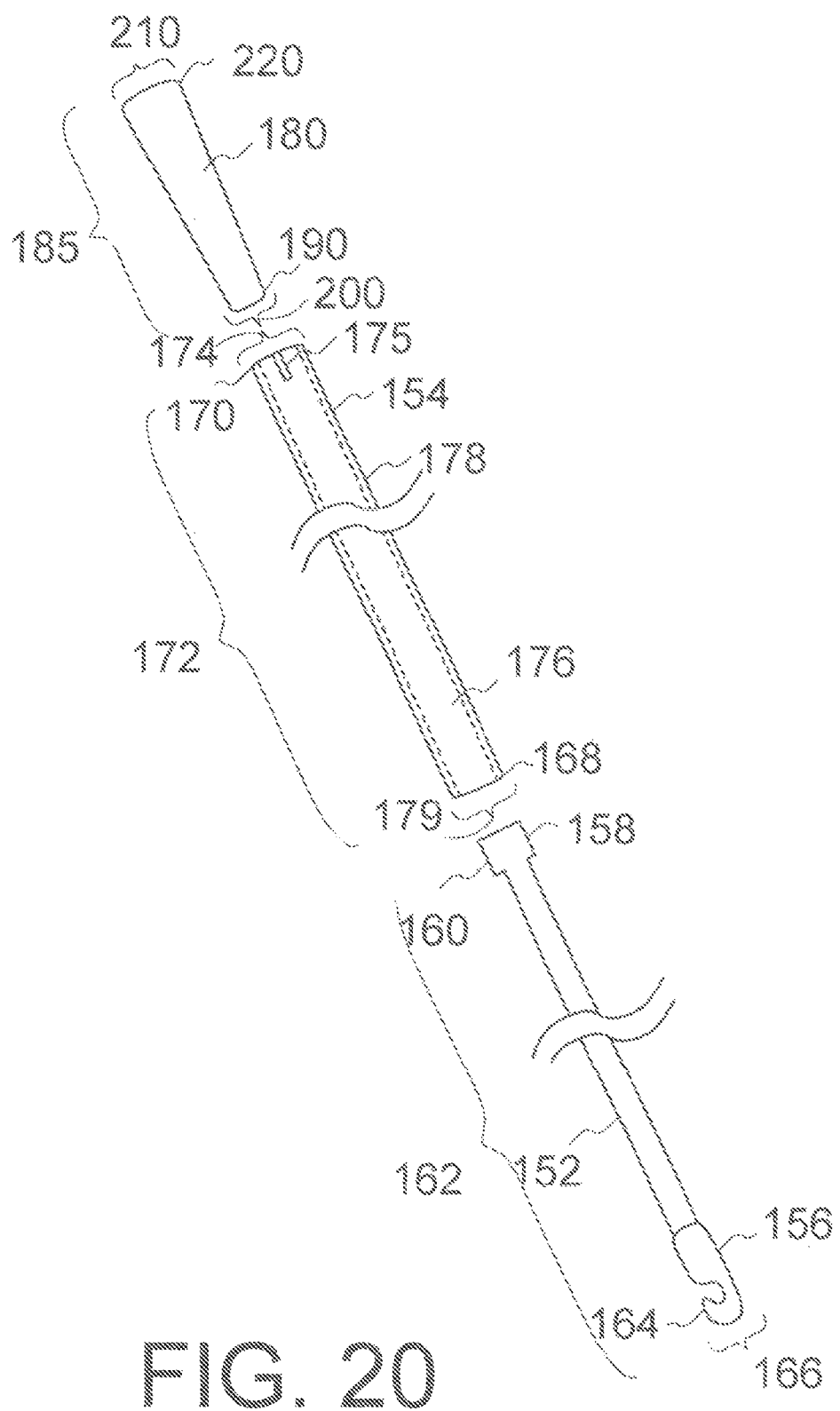
FIG. 20 is generally an illustration depicting a snare, a sheath, and a plug in accordance with a preferred embodiment of the current invention.
Figure 21:
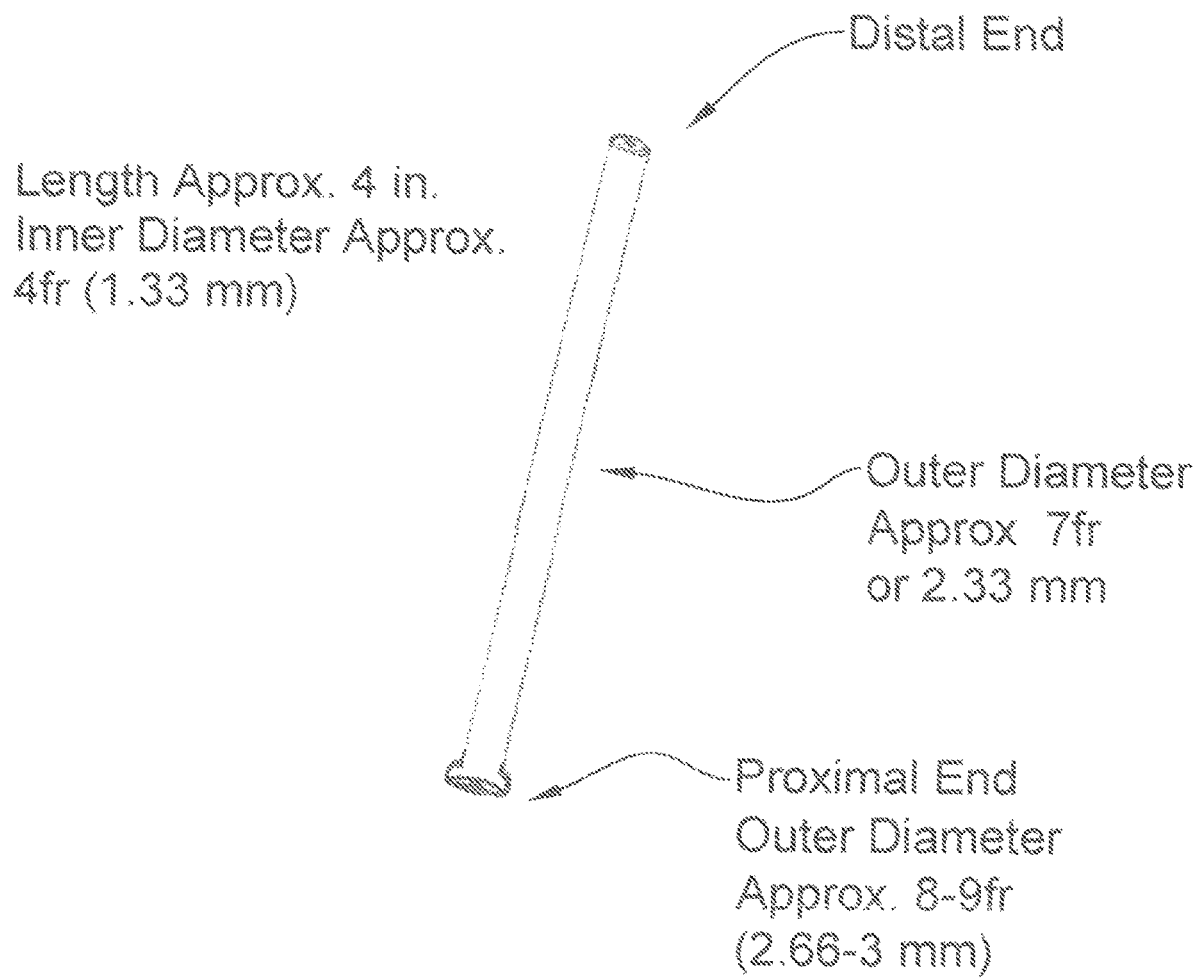
FIG. 21 is a hemostasis device constructed in accordance with alternative embodiments of this invention.

Referring to the drawings and more in particular to FIG. 20, snare 152 may have a proximal and or first end 156 and a distal and or second end 158. It is contemplated that second end 158 may generally be adapted for grabbing, holding and or pulling and may include a loop, ring, handle and or grip 160, which may be utilized with a finger and or thumb. It is understood that numerous other configurations are contemplated other than grip 160 as known. It is contemplated that grip 160 may be plastic, rubber and so forth attached to snare 152. It is understood that snare 152 may be metal, plastic and so forth and grip 160 may be incorporated into second end 158 during manufacture and or provided separately and used as desired.

Snare 152 may have a shaft and or length 162 generally defined as the area and or distance between first end 156 and second end 158. First end 156 may include hook 164. It is contemplated that snare 152 may be about 6 inches in length although it is to be understood that shorter and or longer lengths are also contemplated. Snare 152 may have an outer diameter 166 such as but not limited to three French and or 1 millimeter. Snare 152 may be made from but is not limited to stainless steel. Sheath 154 may have a proximal tip and or first end 168, a distal and or second end 170, a length 172, an outer diameter 174 and an interior passageway 176. Sheath 154 is generally a hollow tube that allows snare 152 to travel there through as desired. First end 168 may be generally oval shaped, round, and combinations thereof to essentially correspond with the puncture and may include a hemostasis material such as but not limited to surgical fabric. Length 172 may be but is not limited to 4 inches although greater and lesser lengths are contemplated.

It is contemplated that second end 170 may include a suture retaining slit 175 generally beginning at the most distal aspect of an inner diameter and or lumen 176 and extending proximally into outer surface 178 of sheath 154. Slit 175 may be but is not limited to 3 millimeters although greater and lesser lengths are also contemplated. It is understood that tool 150 may not utilize slit 175 as discussed further below. Inner diameter 180 may be 4 French and or 1.33 millimeters although numerous other sizes greater and smaller are contemplated. Sheath 154 may be made from plastic although numerous other materials are also contemplated. It is contemplated to utilize an FDA approved, medical grade polymer.

Invention also contemplates that sheath 154 may be of a size to correspond to the size of the introduced catheter thereby allowing a proper and or more accurate fit as sheath 154 is applied to the puncture site. It is understood that tool 150 may include a kit of different sized snares 152, sheaths 154 and or combinations thereof.

Tool 150 still also contemplates utilizing a suture retaining plug 180. The suture retaining plug 180 may be inserted in the distal end 170 of the sheath 154 upon retrieval of the suture 181 and removal of the snare 152 in order to retain the tautness of the suture 181 and hold direct pressure via the sheath 154 on the puncture site of the artery and or vessel. The suture retaining plug 180 may have a length 185 and length 185 may be approximately 1½ inches in length. It is understood that other lengths are contemplated. Suture retaining plug 180 may be tapered in size. Suture retaining plug 180 proximal end 190 may be small enough in first diameter 200 to insert into the distal end 170 of the sheath 154 and gradually getting larger in second diameter 210 towards its distal end 220 in order to create interference with the plug 180 and distal end 170 of the sheath 154, which may hold the suture 181 taut and the sheath 154 in place while providing direct pressure on the puncture site of the vessel creating hemostasis.

In Operation

Tool 150 contemplates a manual compression pressure device, system, and method that may be used in conjunction with a known and unknown vessel closing device such as but not limited to a trademarked PERCLOSE vessel closure device manufactured by PERCLOSE Inc. Upon deployment of the vessel closure device and removal thereof, the current invention may be utilized.

In a preferred embodiment, tool 150 may be utilized by first inserting snare 152 into sheath 154 through second end 170 until hook 166 of snare 152 is generally extending through the first end 168 of sheath 154. It is understood that snare 152 may be provided already inserted into sheath 154.

It is contemplated to hook the suture 181 near the distal end of the suture with hook 166 of snare 152 and retract snare 152 into sheath 154 until hook 164 of snare 152 is no longer visible. It is contemplated to gently advance sheath 154 towards the patient while holding snare 152 in the same position until snare 152 is completely removed from sheath 154 the suture 181 has been pulled through sheath 154 and out second end 170.

It is then contemplated to hold the suture 181 taut while gently advancing sheath 154 through the puncture site in the skin until it seats firmly against the accessed vessel wall and then while holding the suture 181 taut, push the suture 181 into retaining slit 175 of sheath 154 insuring that the suture 181 is firmly immobilized. In another preferred embodiment, tool 150 may not utilize slit 175, but may use plug 180 to trap suture 181. It is understood that tool 150 may utilize both slit 175 and plug 180.

Pressure is now applied such that sheath first end 168 is generally aligned over vessel puncture site pending proper and or desired hemostasis. Hemostasis material may be in a compression position against the puncture site although it is understood that material may not be utilized. After proper hemostasis, it is then contemplated to cut suture 181 at and or near the puncture site. In accordance with a preferred embodiment, sheath 154 may be removed before suture 181 is cut.

It is therefore contemplated that tool 150 may be a postoperative compression device adapted to provide direct pressure to puncture site of vessel utilizing existing suture 181 originating in said vessel and out said puncture site comprising sheath 154 having proximal end 168, length 1172, distal end 170, and interior passageway 176 along said length 172 and said interior passageway 176 having diameter 179; snare 152 removably positioned in said interior passageway 176 of said sheath 154 and said snare 152 having proximal end 156 with hook 164 adapted to hook said suture 181, length longer than said length of said sheath 154, and distal end; and plug 180 having length 185, proximal end 190 having first diameter 200, distal end 220 having second diameter 210 larger than said first diameter 200, and wherein said plug 180 is adapted to secure said proximal end 190 of said plug 180 in said distal end 170 of said sheath 154 for trapping said suture 181 in said sheath 154 after said snare 152 is removed from said sheath 154.

Accordingly, other implementations are within the scope of the following claims. Changes may be made in the combinations, operations, and arrangements of the various parts and elements described herein without departing from the spirit and scope of the invention.

What is claimed:

1. A method for percutaneously closing a puncture through the wall of an artery, comprising:
inserting a guide wire through a percutaneous entry and into the artery;
using the guide wire to guide an insertion of an introducer catheter into the artery;
inserting a balloon catheter through the introducer catheter and into the artery;

locking a firing mechanism loaded with fasteners onto the introducer catheter, thereby aligning the puncture with a distal working end of the firing mechanism;

activating the firing mechanism to fire two or more fasteners onto the artery, each fastener individually tethered to a suture;

percutaneously tying the sutures together to draw the fasteners together, closing the puncture.

\* \* \* \* \*